United States Patent
Ha et al.

(10) Patent No.: US 11,001,503 B2
(45) Date of Patent: May 11, 2021

(54) MFI ZEOLITE WITH MICROPOROUS AND MESOPOROUS HIERARCHICAL STRUCTURE, PREPARATION METHOD THEREFOR, AND CATALYTIC USE THEREOF

(71) Applicant: SOGANG UNIVERSITY RESEARCH FOUNDATION, Seoul (KR)

(72) Inventors: Kyoung-Su Ha, Incheon (KR); Kwang Min Kim, Seoul (KR); Jong Hyun Jeon, Seoul (KR); Choongik Kim, Seoul (KR); Daegak Kim, Seoul (KR)

(73) Assignee: Sogang University Research Foundation, Seoul (KR)

( * ) Notice: Subject to any disclaimer, the term of this patent is extended or adjusted under 35 U.S.C. 154(b) by 151 days.

(21) Appl. No.: 16/470,124

(22) PCT Filed: Dec. 14, 2017

(86) PCT No.: PCT/KR2017/014717
§ 371 (c)(1),
(2) Date: Aug. 8, 2019

(87) PCT Pub. No.: WO2018/110998
PCT Pub. Date: Jun. 21, 2018

(65) Prior Publication Data
US 2019/0359493 A1 Nov. 28, 2019

(30) Foreign Application Priority Data
Dec. 14, 2016 (KR) .................. 10-2016-0170463

(51) Int. Cl.
*C01B 39/40* (2006.01)
*B01J 29/40* (2006.01)
(Continued)

(52) U.S. Cl.
CPC .............. *C01B 39/40* (2013.01); *B01J 29/40* (2013.01); *B01J 37/10* (2013.01); *C07C 2/48* (2013.01);
(Continued)

(58) Field of Classification Search
None
See application file for complete search history.

(56) References Cited

U.S. PATENT DOCUMENTS

| 4,636,373 A | * | 1/1987 | Rubin | .................... B01J 29/035 |
| | | | | 423/332 |
| 4,640,829 A | * | 2/1987 | Rubin | .................. B01J 29/7023 |
| | | | | 423/277 |

(Continued)

FOREIGN PATENT DOCUMENTS

| CN | 101723403 A | * | 6/2010 |
| JP | 2008-266149 A | | 11/2008 |

(Continued)

OTHER PUBLICATIONS

CN101723403A English Translation obtained from Espacenet, Dec. 22, 2020, pp. 1-7. (Year: 2020).*

*Primary Examiner* — Philip Y Louie
(74) *Attorney, Agent, or Firm* — Seed IP Law Group LLP (57) ABSTRACT

The present invention relates to a method of preparing an MFI zeolite with a microporous and mesoporous hierarchical structure in which a non-benzene-based first structure-directing agent, which provides ordered microporous pore sizes and a framework of MFI zeolite seed crystals, and a second structure-directing agent containing one benzene ring and an ammonium ion, which functions as a mesopore-directing agent without interfering with the function of the first structure-directing agent, are simultaneously used; an MFI zeolite with a microporous and mesoporous hierarchical structure, which is prepared by the method, and a catalyst (Continued)

Conventional ZSM-5　　HCZ-1 use thereof for a reaction of converting acetylene into an aromatic compound; and a method of preparing an aromatic compound from acetylene using the catalyst.

17 Claims, 5 Drawing Sheets

(51) Int. Cl.
    *C07C 2/48* (2006.01)
    *B01J 37/10* (2006.01)
    *C07C 15/04* (2006.01)
    *C07C 15/06* (2006.01)
    *C07C 15/08* (2006.01)

(52) U.S. Cl.
    CPC ...... *C01P 2002/72* (2013.01); *C01P 2006/16* (2013.01); *C07C 15/04* (2013.01); *C07C 15/06* (2013.01); *C07C 15/08* (2013.01)

(56) References Cited

U.S. PATENT DOCUMENTS

| | | | |
|---|---|---|---|
| 6,022,519 A * | 2/2000 | Shimizu | B01J 29/035 423/335 |
| 2013/0052125 A1* | 2/2013 | Moini | B01J 29/7015 423/700 |
| 2017/0158520 A1* | 6/2017 | Xie | B01J 37/0018 |
| 2019/0330071 A1* | 10/2019 | Cho | F01N 3/2066 |

FOREIGN PATENT DOCUMENTS

| | | |
|---|---|---|
| JP | 2012-62234 A | 3/2012 |
| KR | 10-0263280 B1 | 7/2000 |
| KR | 10-2015-0075813 A | 7/2015 |
| KR | 10-2015-0091518 A | 8/2015 |
| KR | 10-2016-0005054 A | 1/2016 |

* cited by examiner

Summarized scheme

Detail scheme

[FIG. 5]

MFI ZEOLITE WITH MICROPOROUS AND MESOPOROUS HIERARCHICAL STRUCTURE, PREPARATION METHOD THEREFOR, AND CATALYTIC USE THEREOF

BACKGROUND OF THE INVENTION

1. Technical Field

The present invention relates to a method of preparing an MFI zeolite with a microporous and mesoporous hierarchical structure in which a non-benzene-based first structure-directing agent, which provides ordered microporous pore sizes and a framework of MFI zeolite seed crystals, and a second structure-directing agent containing one benzene ring and an ammonium ion, which functions as a mesopore-directing agent without interfering with the function of the first structure-directing agent, are simultaneously used; an MFI zeolite with a microporous and mesoporous hierarchical structure, which is prepared by the method, and a catalyst use thereof for a reaction of converting acetylene into an aromatic compound; and a method of preparing an aromatic compound from acetylene using the catalyst.

2. Description of the Related Art

As a result of the development of alternative energy resources due to limited reserves of fossil fuels and global warming caused by CO2, catalyst conversion technologies using natural gas or shale gas with low greenhouse gas emissions have been continuously developed worldwide. Further, carbon-neutral and renewable alternative energy resources are ultimately required. Thus, efforts have been made to produce materials that can replace petroleum products using raw materials derived from plant resources. As such efforts, technologies of synthesizing acetylene from shale gas, which has abundant reserves and emits a small amount of greenhouse gases, or biomass, which emits almost no greenhouse gases, by using a catalytic reaction have been developed. Methods of converting the acetylene produced in this way into an aromatic compound such as xylene, which is a raw material of synthetic fibers, or benzene or toluene, which are typical raw materials for chemical products, have been researched as important technologies for producing high value-added compounds. For example, polyethylene terephthalate (PET) is one of the most productive petrochemical products, and polyester fibers, which use PET as a raw material, are produced in an amount of about 40 million tons per year globally. Accordingly, the production of xylene or the like, which is a raw material for polyethylene terephthalate, from a biomass-derived raw material is not only environmentally friendly, but also approaches the realization of a sustainable low-carbon society.

Zeolites collectively refer to crystalline aluminosilicates having Angstrom-sized pores and channels in their crystal lattices. Zeolites are microporous materials, and are aluminosilicate mineral materials widely used as adsorbents or catalysts. Zeolites may occur naturally or may be synthesized artificially, may have a unique structure and pore size depending on the kind, and may be converted in a desired direction depending on the method of preparation. Since zeolites have a constant pore size, they may act as a molecular sieve for separating materials depending on pore size. When a zeolite is used as a catalyst, it may exhibit excellent activity, low activity, or no activity depending on the pore size of the zeolite itself and the size of a reactant or a product, even for similar reactions. Another factor influencing catalytic activity is the composition ratio of silicon and aluminum.

Since aluminosilicates have a negative charge at the site of aluminum in their framework, cations for charge cancellation are present in the pores, and the remaining space in the pores may usually be filled with water molecules. The structure, shape, and size of the three-dimensional pores of zeolites change depending on the kind of zeolite, but the diameter of the pores usually corresponds to the size of molecules. Accordingly, zeolites are called a molecular sieve because depending on the kind, they have size selectivity or shape selectivity for molecules charged into the pores. As described above, zeolites have acidic sites in the pores, and each of the acidic sites may exhibit catalytic activity. Therefore, each of the pores may act like a small reaction group capable of performing an acidic catalytic reaction therein based on such catalytic activity and the aforementioned selectivity.

Meanwhile, there are known zeolite-like quasi-molecular sieves in which a part or all of silicon or aluminum is replaced with various other elements instead of the silicon (Si) and aluminum (Al) constituting the zeolite framework structure. For example, there is an AlPO4-based molecular sieve in which completely aluminum-removed porous silicalite and silicon are replaced with phosphorus (P), and a quasi-molecular sieve which is obtained by partially substituting the zeolite framework with various metal elements such as Ti, Mn, Co, Fe, and Zn. Although these zeolite-derived molecular sieves do not belong to zeolites according to the original mineralogical classification, all of these molecular sieves are called zeolites in the art. Thus, these quasi-molecular sieves are included in the scope of the present invention without limitation as long as they maintain an MFI structure.

Figure 5:
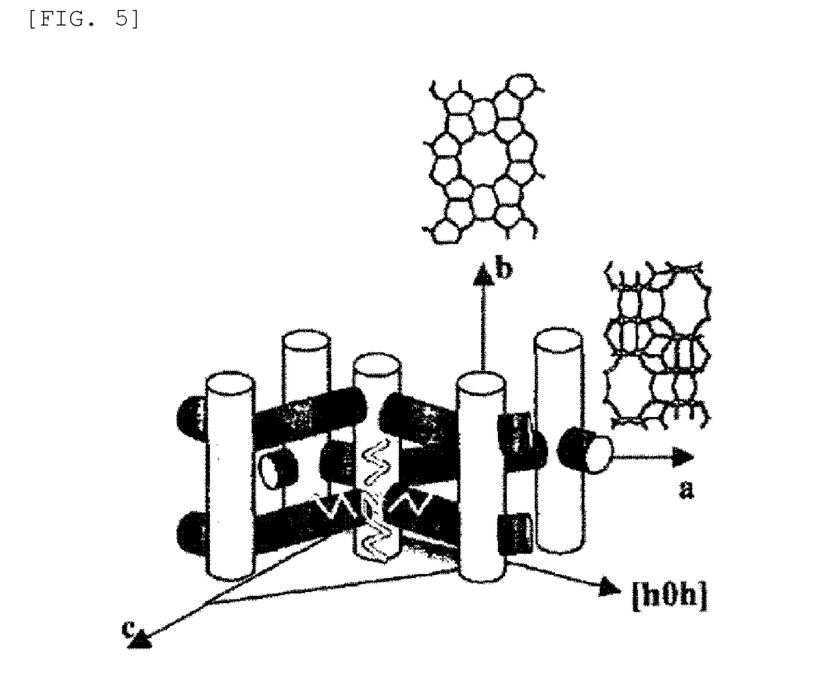
FIG. 5 schematically shows a crystal having an MFI structure into which a structure-directing agent is inserted.

The MFI structure is shown in FIG. 5. In the case of this zeolite, a channel in which elliptical pores (0.51 nm×0.55 nm) are connected in a zigzag form flows in the a-axis direction, and approximately circular pores (0.54 nm×0.56 nm) linearly extend in the b-axis direction to form a linear channel. The channel is not open in the c-axis direction. As described above, in the case of the MFI-type zeolite, the pore shape, pore size, and channel structure thereof change depending on crystal orientation.

Powdered MFI zeolite is widely used as a crude oil cracking catalyst, an adsorbent, a dehydrating agent, an ion exchanger, a gas purifier, or the like in real-world and industrial settings, whereas an MFI zeolite thin film formed on a porous substrate such as porous alumina is widely used as a molecular separation film capable of separating molecules according to size. In addition, the MFI zeolite thin film is widely applied to secondary and tertiary nonlinear optical thin films, three-dimensional memory materials, solar energy collectors, electrode-assisting materials, semiconductor quantum dot and quantum wire carriers, molecular circuits, photosensitizers, illuminants, low-dielectric thin films, anti-rust coating agents, and the like.

Since ZSM-5 itself, which is a kind of MFI zeolite, exhibits excellent catalytic properties such as stability and acidic sites, while including only micropores, the reactions capable of utilizing the ZSM-5 as a catalyst are limited. Specifically, the ZSM-5, which is zeolite catalyst having micropores, is advantageous in that it has a large surface area and strong acidic sites and exhibits excellent hydrothermal stability, but is disadvantageous in that facile mass transfer is limited and its catalytic application field is limited.

Therefore, research on catalysts having mesopores has been conducted. As the materials having mesopores, materials such as MCM-41 and SBA-15 have been developed. However, since these materials have only a mesoporous structure, there is a problem in that they have low selectivity and low stability due to the change in Si/Al ratio.

SUMMARY OF THE INVENTION

The inventors of the present invention have found that in the case of a cationic surfactant containing one benzene ring and an ammonium ion, which are structure-directing agents for forming mesopores and are connected to a bivalent alkyl group or alkoxy group, when MFI zeolite is hydrothermally synthesized in combination with a non-benzene-based structure-directing agent providing ordered microporous pore sizes and a framework of MFI zeolite seed crystals, it is possible to provide an MFI zeolite with a hierarchical structure in which an ordered microporous MFI zeolite additionally has mesopores, and they have found that an MFI zeolite with a microporous and mesoporous hierarchical structure exhibits excellent activity in the reaction of synthesizing an aromatic compound from acetylene, and is particularly useful for the preparation of xylene. Based on these findings, the present invention has been completed.

A first aspect of the present invention provides a method of preparing an MFI zeolite with a microporous and mesoporous hierarchical structure in which an ordered microporous MFI zeolite additionally has mesopores, the method including: a first step of preparing a first aqueous solution in which a non-benzene-based first structure-directing agent, providing ordered microporous pore sizes and a framework of MFI zeolite seed crystals, is dissolved in water; a second step of preparing a second(2) aqueous solution in which a cationic surfactant, as a second structure-directing agent, containing one benzene ring and an ammonium ion connected to a bivalent alkyl group or alkoxy group, is dissolved in water; a third step of mixing an aluminum precursor with the second aqueous solution to prepare a second'(2') aqueous solution; a fourth step of sequentially adding a silica precursor and the second' aqueous solution to the first aqueous solution to prepare a mixed solution; and a fifth step of hydrothermally crystallizing the mixed solution obtained in the fourth step.

A second aspect of the present invention provides an MFI zeolite with an ordered microporous and mesoporous hierarchical structure, prepared by the method of the first aspect.

A third aspect of the present invention provides an acidic catalyst composition, including the MFI zeolite with an ordered microporous and mesoporous hierarchical structure as an active ingredient.

A fourth aspect of the present invention provides a method of preparing an aromatic compound, a derivative thereof, or a product prepared using the aromatic compound or the derivative thereof as an intermediate from acetylene in the presence of the acidic catalyst composition, the method including forming an aromatic compound from acetylene.

Hereinafter, the present invention will be described in more detail.

A conventional MFI zeolite is an aluminosilicate zeolite belonging to zeolites of the pentasil family, and is a material developed as a heterogeneous catalyst for a hydrocarbon isomerization reaction for use in the petroleum industry. For example, the MFI zeolite may include three or four pentasil units connected to each other through an oxygen bridge to form a pentasil chain. In this case, the pentasil unit includes eight five-membered rings, each vertex of the pentasil unit is aluminum or silicon, oxygen is bonded between these vertexes, and the pentasil chains are thus connected to each other through the oxygen bridge to form a corrugated sheet having ten ring holes. ZSM-5, which is a kind of MFI zeolite, may be hydrothermally synthesized by reacting silicon oxide and sodium aluminate at high temperature and high pressure in the presence of a tetraalkylammonium compound. The MFI zeolite is known to exhibit activity for an acidic catalyst reaction such as hydrocarbon isomerization or hydrocarbon alkylation, but is not known to exhibit catalytic activity for a reaction of converting acetylene into an aromatic compound.

An ordered microporous zeolite is advantageous in terms of a large surface area, strong acidic sites, and excellent hydrothermal stability, but is disadvantageous in that facile mass transfer is inhibited, restricting its application as a catalyst.

Meanwhile, MCM series (MCM-41, MCM-48, and MCM-50) or SBA series (SBA-15), which are mesoporous materials having a non-crystalline framework, have low acidic sites and poor hydrothermal stability in spite of large pores, and thus practical application thereof is limited.

In order to solve the above problems, the present invention intends to provide an MFI zeolite with a hierarchical structure in which an ordered microporous MFI zeolite additionally has mesopores, and the MFI zeolite with a hierarchical structure may be prepared through the following steps.

These steps include a first step of preparing a first aqueous solution in which a non-benzene-based first structure-directing agent, providing ordered microporous pore sizes and a framework of MFI zeolite seed crystals, is dissolved in water; a second step of preparing a second aqueous solution in which a cationic surfactant, as a second structure-directing agent, containing one benzene ring and an ammonium ion connected to a bivalent alkyl group or alkoxy group, is dissolved in water; a third step of mixing an aluminum precursor with the second aqueous solution to prepare a second' aqueous solution; a fourth step of sequentially adding a silica precursor and the second' aqueous solution to the first solution to prepare a mixed solution; and a fifth step of hydrothermally crystallizing the mixed solution obtained in the fourth step.

The mesopore volume (cm3/g) of the MFI zeolite with a microporous and mesoporous hierarchical structure according to the present invention is two times or more, preferably three times or more, and more preferably four times or more, as compared with a microporous MFI zeolite (refer to Table 1).

For example, the MFI zeolite may be a zeolite selected from the group consisting of ZSM-5, silicalite, TS-1, AZ-1, Bor-C, boracite C, encilite, FZ-1, LZ-105, monoclinic H-ZSM-5, mutenite, NU-4, NU-5, TSZ, TSZ-III, TZ-01, USC-4, USI-108, ZBH, and ZKQ-1B. Specifically, the MFI zeolite may be a ZSM-5 zeolite, but is not limited thereto.

The structure-directing agent is a material acting as a template of a specific crystalline structure, and the charge distribution, size, and geometric shape of the structure-directing agent provide structure-directing properties.

In the present invention, the first structure-directing agent uses a non-benzene-based structure-directing agent capable of forming seed crystals having an MFI structure as a seed structure-directing agent. Since the seed structure-directing agent induces a crystal nucleation reaction, it is not preferred that the seed structure-directing agent be used as a structure-directing agent for a secondary growth method.

For example, the non-benzene-based first structure-directing agent may be tetraalkylammonium hydroxide (here, alkyl is $C_{1-4}$ alkyl).

For example, since the tetraalkylammonium hydroxide is commercialized and sold, commercially available tetraethylammonium hydroxide or tetrapropylammonium hydroxide may be used. Considering the economic efficiency of processes, tetrapropylammonium hydroxide, which is a relatively cheap material, may be used, but the present invention is not limited thereto.

Meanwhile, a template method is frequently used to produce a porous material having mesopores of 50 nm or less. For example, heat treatment is performed using a surfactant having a long chain as a template to convert a template space into pores, thereby producing a porous oxide.

The present invention is characterized in that a cationic surfactant, as a second structure-directing agent acting as a mesopore-directing agent, containing one benzene ring and an ammonium ion connected to a bivalent alkyl group or alkoxy group is used together with the non-benzene-based first structure-directing agent capable of forming seed crystals having an MFI structure.

For example, the second structure-directing agent may be a compound represented by Formula 1 below:

[Formula 1]

wherein, in Formula 1, X is Br, F, I, or Cl, L is —O— or a direct bond, and $1 \leq n \leq 6$, preferably, $1 \leq n \leq 4$ is satisfied.

For example, the second structure-directing agent of Formula 1 may be halogenated benzyltrimethylammonium represented by Formula 1-1 below, and, specifically, may be benzyltrimethylammonium bromide in which X is Br. However, examples thereof are not limited thereto.

[Formula 1-1]

In Formula 1-1, X is Br, F, I, or Cl.

The second structure-directing agent of the present invention may not prevent the first structure-directing agent from providing a framework of MFI zeolite seed crystals of ordered microporous pore sizes, and may serve as a mesopore-directing agent. When the MFI zeolite is hydrothermally synthesized by using both the first structure-directing agent and the second structure-directing agent, there may be provided an MFI zeolite with a hierarchical structure in which an ordered microporous MFI zeolite additionally has mesopores.

In the method according to the present invention, as the silica precursor and the aluminum precursor, a general silica precursor and a general aluminum precursor, which are used in the preparation of MFI commonly known in the art, may be used without limitation. For example, the silica precursor may be tetraethyl orthosilicate (TEOS), glass water, fumed silica, or colloidal silica, and the aluminum precursor may be sodium aluminate, aluminum isopropoxide, aluminum oxide, or aluminum hydroxide.

In the method according to the present invention, the following compounds supplying elements other than silicon constituting MFI crystals may further be added:

1) all kinds of F-containing materials, such as HF, $NH_4F$, NaF, and KF; and/or 2) materials used in inserting different kinds of elements other than aluminum and silicon into a framework (for example, transition metals such as titanium, group 13 elements such as gallium, and group 14 elements such as germanium).

It is preferable that the ratio of the additional raw material be limited to the range of 0.1 to 30.

In the method according to the present invention including the first to fifth steps, there may be provided an MFI zeolite with a hierarchical structure, as a novel catalyst, which maintains excellent catalytic characteristics such as thermal stability and acidic sites of a conventional MFI zeolite and additionally provides mesopores to overcome the disadvantage of limited catalytic application due to the restriction of mass transfer.

In this case, the distribution and/or size of mesopores may be adjusted by the content of the additionally used second structure-directing agent (for example, halogenated benzyltrimethylammonium), and the mass transfer in the process of reactants reaching active sites and/or the process of discharging reaction products from active sites to the outside of a catalyst may be facilitated by adjusting the size of mesopores to prevent the reduction of catalytic activity due to the restriction of mass transfer. That is, when the amount of the second structure-directing agent used is adjusted, the pore size of the synthesized MFI zeolite with a hierarchical structure may be adjusted to a level that facilitates mass transfer according to the kind of reactants and/or products.

Figure 2:
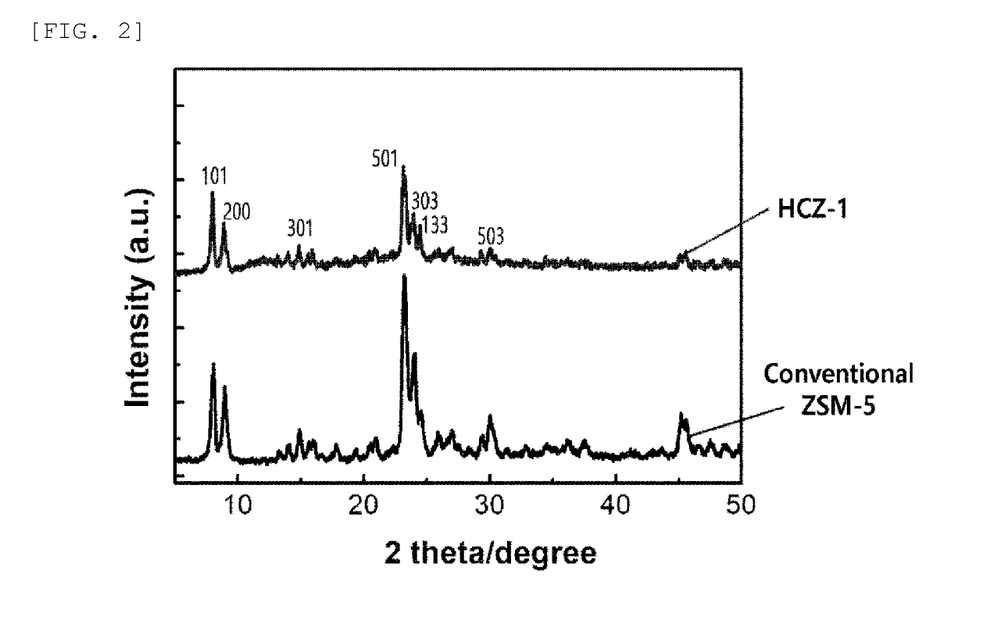
FIG. 2 shows the XRD analysis results of the ZSM-5 zeolite (marked as HCZ-1) having a hierarchical structure according to the present invention, in which conventional ZSM-5 zeolite is used as a control group.

In an embodiment of the present invention, when benzyltrimethylammonium bromide, as an additional structure-directing agent, was included or not included in tetrapropylammonium hydroxide, which is a structure-directing agent generally used in MFI zeolite, to prepare ZSM-5 zeolites and X-ray diffraction patterns thereof were compared with each other, it was found that the ZSM-5 zeolite synthesized by the method of the present invention includes unique peaks appearing in the conventional ZSM-5 zeolite, and thus it can be ascertained that the ZSM-5 zeolite synthesized by the method of the present invention includes micropores of the ZSM-5 zeolite itself (refer to FIG. 2).

Specifically, the tetraalkylammonium hydroxide as the first structure-directing agent and the halogenated benzyltrimethylammonium as the second structure-directing agent are used at a weight ratio of 1:(0.1 to 5). When the weight ratio of the tetraalkylammonium hydroxide and the halogenated benzyltrimethylammonium is less than 1:0.1, the development of mesopores may be inhibited, and when the weight ratio thereof is more than 1:5, the development of mesopores may be inhibited, and thus desirable catalytic properties of the MFI zeolite itself may be lost.

The MFI zeolite of the present invention may be prepared at a molar ratio of tetraethyl orthosilicate as the silica precursor sodium aluminate as the aluminum precursor: tetraalkylammonium hydroxide as the first structure-directing agent:benzyltrimethylammonium bromide as the second structure-directing agent:water of (30 to 35):(0.7 to 1.3):(5 to 10):(10 to 15):(1100 to 1200), but the present invention is not limited thereto. When the molar ratio of the raw materials cannot be maintained, it may be difficult to synthesize an MFI zeolite with a developed microporous and mesoporous hierarchical structure to be attained.

For example, the fifth step may be performed at a temperature ranging from 150° C. to 250° C. for 12 hours to 48 hours. However, the present invention is not limited thereto, and the fifth step may be performed by using a hydrothermal crystallization condition and/or method used in the preparation of conventional MFI zeolites.

Moreover, the method according to the present invention may further include the steps of: washing, drying or sintering the crystals obtained from the fifth step, or combining two or more steps selected therefrom. However, the present invention is not limited thereto, and each of the steps may be performed using conventional washing, drying, and firing methods known in the art. For example, the washing step may be performed by filtering the crystals with a lower alcohol such as ethanol, and the drying step may be performed by leaving the washed crystals overnight at 100° C. or higher, for example, 110° C., but the present invention is not limited thereto. The sintering step may be performed at 500° C. or higher, for example, 550° C., but the present invention is not limited thereto.

The MFI zeolite with a microporous and mesoporous hierarchical structure prepared according to the method of the present invention may have a molar ratio of Si/Al of 20 to 150, and specifically a molar ratio of Si/Al of 30 to 35. However, the present invention is not limited thereto, and the molar ratio thereof is not limited as long as the MFI zeolite has a microporous and mesoporous hierarchical structure.

The MFI zeolite with a microporous and mesoporous hierarchical structure prepared according to the method of the present invention may be a cubic particle in which each side has a deviation of less than 10% in length. For example, the MFI zeolite of the present invention prepared in this way may be a cubic particle having a horizontal length of 3 μm to 10 μm, a vertical length of 3 μm to 10 μm, and a height of 3 μm to 10 μm, but is not limited thereto.

In another aspect of the present invention, there is provided an acidic catalyst composition including the MFI zeolite with the aforementioned ordered microporous and mesoporous hierarchical structure as an active ingredient. For example, the acidic catalyst composition according to the present invention may be used in a conversion reaction of acetylene into an aromatic compound.

The present inventors have found that the MFI zeolite with a microporous and mesoporous hierarchical structure according to the present invention has a catalytic activity for the conversion reaction of acetylene into an aromatic compound. For example, the aromatic compound that can be synthesized from acetylene by using the catalyst composition of the present invention may be benzene, toluene, or xylene. Specifically, the catalyst composition of the present invention may be useful for the synthesis of xylene, but the kind of the aromatic compound that can be synthesized by using this catalyst composition is not limited thereto.

In still another aspect of the present invention, there is provided a method of preparing an aromatic compound from acetylene, a derivative thereof, or a product prepared by using the aromatic compound or the derivative thereof as an intermediate, the method including: forming an aromatic compound from acetylene in the presence of the aforementioned acidic catalyst composition.

As described above, since the MFI zeolite with a microporous and mesoporous hierarchical structure according to the present invention has excellent catalytic activity for the conversion reaction of acetylene into an aromatic compound, an aromatic compound such as benzene, toluene, or xylene may be synthesized by using the catalyst composition including this MFI zeolite as an active ingredient. Specifically, the catalyst composition of the present invention may be useful for the synthesis of xylene, but the kind of the aromatic compound that can be synthesized by using this catalyst composition is not limited thereto.

Further, the product that can be prepared by using the aromatic compound or derivative thereof as an intermediate is also included in the scope of the present invention. The product that can be prepared by using the aromatic compound or derivative thereof as an intermediate is a material prepared through an additional process by using the aromatic compound or derivative thereof prepared using the catalyst of the present invention, and a non-limiting example thereof may include a synthetic polymer having an aromatic moiety such as polyester. The additional process may include transalkylation, hydrocracking, and esterification.

Since the ZSM-5 zeolite with a microporous and mesoporous hierarchical structure according to the present invention maintains the large surface area, acidic sites, and excellent hydrothermal stability of the conventional ZSM-5 zeolite itself and further includes a mesoporous structure, this ZSM-5 zeolite can overcome the disadvantage that mass transfer is restricted in the conventional structure including only micropores, and thus this ZSM-5 zeolite can be used as a catalyst in various reactions. In particular, since this ZSM-5 zeolite exhibits excellent activity for the conversion reaction of acetylene into an aromatic compound, this ZSM-5 zeolite can be usefully used as a catalyst for synthesizing an aromatic compound.

BRIEF DESCRIPTION OF THE DRAWINGS

The above and other objects, features, and advantages of the present invention will be more clearly understood from the following detailed description taken in conjunction with the accompanying drawings, in which.

DESCRIPTION OF THE PREFERRED EMBODIMENTS

Hereinafter, the present invention will be described in more detail with reference to Examples. However, these Examples are only illustrative of the present invention, and the scope of the present invention is not limited to these Examples.

Figure 1:
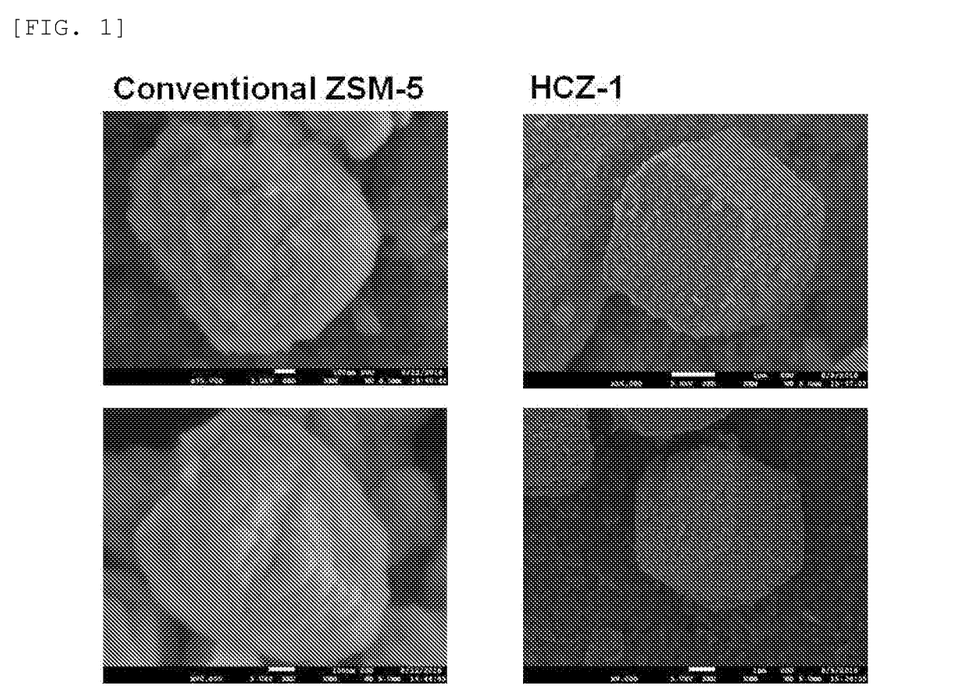
FIG. 1 shows the results of observing the shape of the ZSM-5 zeolite (marked as HCZ-1) having a hierarchical structure according to the present invention by field emission scanning electron microscopy (FE-SEM), in which conventional ZSM-5 zeolite is used as a control group.

Example 1: Preparation of ZSM-5 Zeolite with Hierarchical Structure 2.441 g of 41.7 wt % tetrapropylammonium hydroxide (TPAOH) was added to 8.388 g of water and stirred for 30 minutes to prepare a first solution. Additionally, 1.91 g of benzyltrimethylammonium bromide (BTMAB) was added to 3 g of water to prepare a second solution. Sodium aluminate (NaAlO2) was added to the second solution and mixed by stirring for 30 minutes. Tetraethyl orthosilicate (TEOS) and the second solution were sequentially added to the first solution to prepare a mixed solution. The mixed solution was stirred for about 3 hours until this solution became transparent. The mixed solution was hydrothermally synthesized at 190° C. for 24 hours by using an autoclave. The resultant was filtered and washed with distilled water and ethanol to obtain crystals. The obtained crystals were dried overnight at 110° C., and then sintered at 550° C. In this case, the reactants were used at a molar ratio of TEOS:NaAlO2:TPAOH:BTMAB:H2O of 32:1:8:13:1138. The shape of the synthesized ZSM-5 zeolite with a hierarchical structure was observed by field emission scanning electron microscopy (FE-SEM), and the results thereof are shown in FIG. 1. As shown in FIG. 1, the ZSM-5 zeolite with a hierarchical structure according to the present invention was formed in the shape of a regular cube, and thus this ZSM-5 zeolite was named HCZ-1 (hierarchical cubic zeolite-1).

Comparative Example 1: Preparation of Conventional ZSM-5 Zeolite

A conventional ZSM-5 zeolite was prepared in the same manner as in Example 1, except that benzyltrimethylammonium bromide (BTMAB) was not used. The shape of the ZSM-5 zeolite prepared in this way was observed by FE-SEM, and the results thereof are shown in FIG. 1.

Example 2: Conversion of Synthesized Zeolite to Proton Form (H-Form)

Since each of the zeolites synthesized according to Example 1 and Comparative Example 1 has a sodium-bonded form, the sodium-bonded form is required to be converted to a proton form in order to impart activity as a catalyst, and thus the two kinds of zeolites were treated as follows to be converted to a proton form.

Specifically, the sodium-bonded zeolite prepared according to Example 1, Na-HCZ-1, was added to 30 mL of a 1 M aqueous ammonium sulfate solution, stirred at 70° C. for 24 hours, and then vacuum-filtered with distilled water to be converted into an ammonium form. The process was repeated twice. Then, the zeolite converted to an ammonium form was sintered at 500° C. for 3 hours or more to be converted to a proton form. The conventional zeolite prepared in a sodium form according to Comparative Example 1, conventional Na-ZSM-5, was also converted to a proton form in the same manner.

Experimental Example 1: Analysis of Characteristics of ZSM-5 Zeolite

The zeolites prepared according to Example 1 and Comparative Example 1 and converted to a proton form according to Example 2 were analyzed by XRD, and the results thereof are shown in FIG. 2. As shown in FIG. 2, the ZSM-5 zeolite with a hierarchical structure according to the present invention, HCZ-1, includes an XRD peak inherent to ZSM-5 observed from conventional ZSM-5 zeolite, and this indicates that the microstructure of ZSM-5 is maintained.

Figure 3:
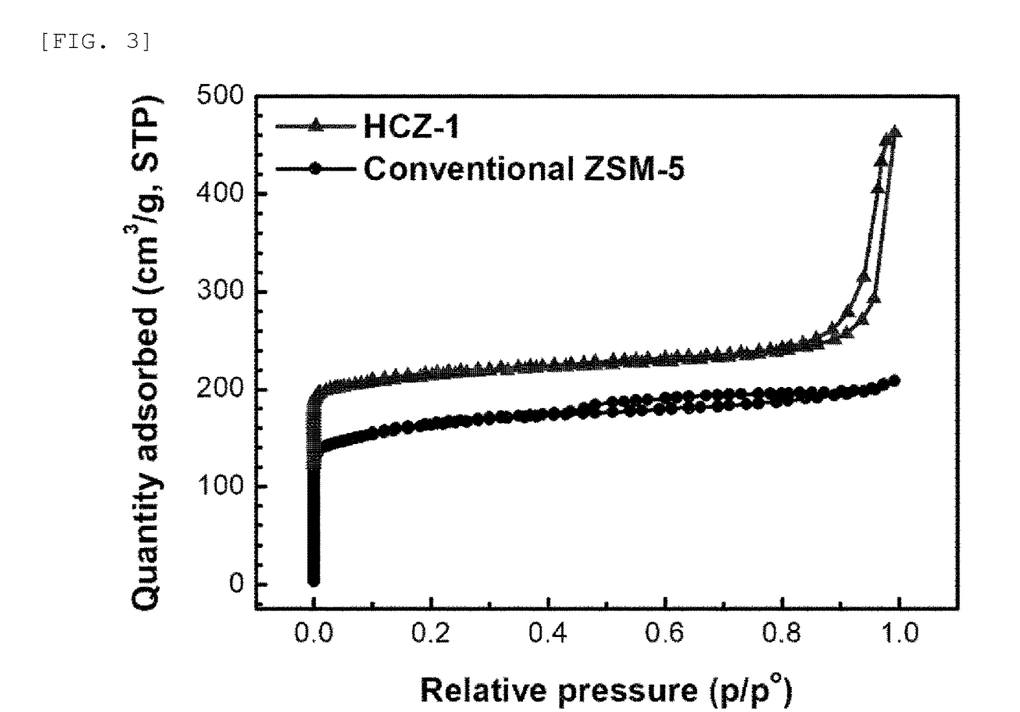
FIG. 3 shows the adsorption amount of the ZSM-5 zeolite (marked as HCZ-1) having a hierarchical structure according to the present invention with respect to relative pressure, in which conventional ZSM-5 zeolite is used as a control group.

Moreover, the adsorbed quantities of the zeolites according to relative pressure were measured as shown in FIG. 3, and the BET surface areas and mesopore volumes of the zeolites were measured and given in Table 1 below. As shown in FIG. 3, the adsorbed quantity of the HCZ-1 having a hierarchical structure was greater than the adsorbed quantity of the conventional ZSM-5 zeolite, and the mesopore volume of the HCZ-1 having a hierarchical structure was remarkably increased as compared with the mesopore volume of the conventional ZSM-5 zeolite.

TABLE 1

|  | Conventional ZSM-5 | HCZ-1 |
|---|---|---|
| BET surface area ($m^2/g$) | 432 | 303 |
| Mesopore volume ($cm^3/g$) | 0.089 | 0.425 |

Experimental Example 2: ZSM-5 Zeolite Catalytic Conversion of Acetylene

Figure 4:
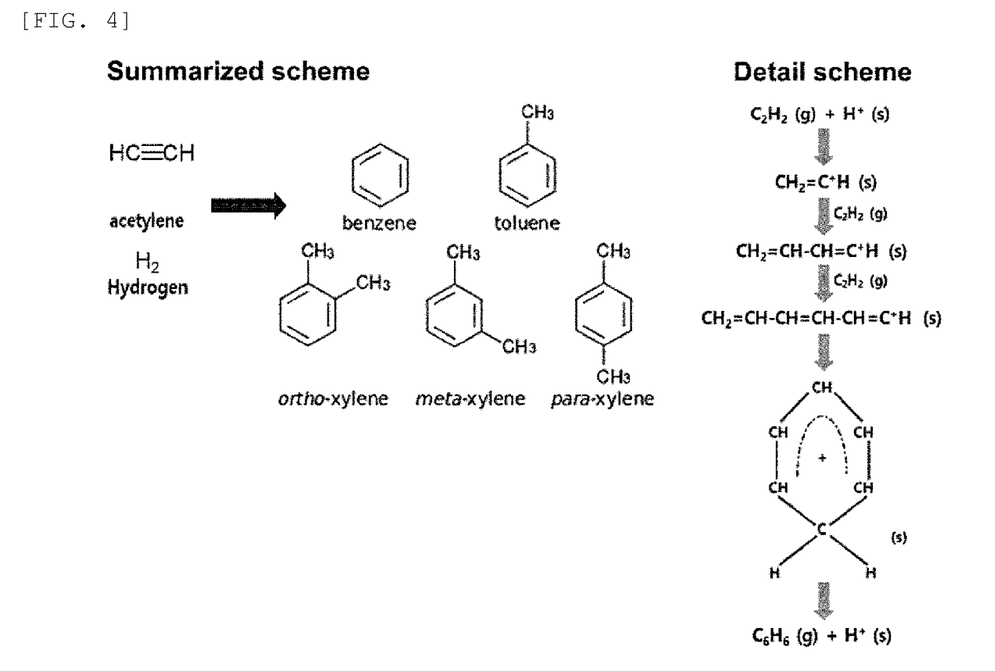
FIG. 4 shows a conversion reaction of acetylene into an aromatic compound using the catalyst according to the present invention.

The acetylene conversion reaction shown in FIG. 4 was performed using each of the zeolites prepared according to Example 1 and Comparative Example 1 and imparted with catalytic activity according to Example 2, and the results thereof were summarized in a series of tables below. The selectivity of a catalytic reaction, yield of each component, and yields of aromatic compounds and total products using the conventional ZSM-5 zeolite were given in order in FIGS. 2 to 4, and those for using the ZSM-5 zeolite (HCZ-1) having a hierarchical structure according to the present invention were given in FIGS. 5 to 7.

Specifically, in the acetylene conversion reaction, acetylene ($C_2H_2$), hydrogen (H2), and nitrogen (N2) as an internal standard were reacted at 400° C. while being injected into a reactor filled with 0.3 g of each of the catalysts at flow rates of 10 sccm, 40 sccm, and 50 ccm, respectively.

The values in the following tables are calculated as follows. For reference, TOS means time on stream.

$$C_2H_2\ input = \frac{C_2H_2\ input - C_2H_2\ output}{C_2H_2\ input}$$

$$Selectivity = \frac{X\ output}{C_2H_2\ input - C_2H_2\ output}$$

In the equations, X indicates $CH_4$, $C_2H_6$, $C_2H_4$, $C_8H_5$, C8H6, benzyl, toluene, or xylene as a product of the acetylene conversion reaction.

Yield of X=$C_2H_2$ conversion rate×selectivity of X

TABLE 2

| TOS (min) | $C_2H_2$ Conversion rate (%) | Selectivity (%) | | | | | | | | |
|---|---|---|---|---|---|---|---|---|---|---|
| | | $CH_4$ | $C_2H_6$ | $C_2H_4$ | $C_3H_8$ | $C_3H_6$ | benzene | toluene | xylene | unknown |
| 0 | 89.19 | 0.01 | 0.01 | 0.61 | 0 | 0.29 | 0.31 | 0.36 | 0.19 | 0.11 |

TABLE 3

| TOS (min) | $C_2H_2$ Conversion rate (%) | Yield (%) | | | | | | | | |
|---|---|---|---|---|---|---|---|---|---|---|
| | | $CH_4$ | $C_2H_6$ | $C_2H_4$ | $C_3H_8$ | $C_3H_6$ | benzene | toluene | xylene | unknown |
| 0 | 89.19 | 0.01 | 0.01 | 0.54 | 0 | 0.26 | 0.28 | 0.32 | 0.17 | 0.09 |

TABLE 4

| Temperature and specimen conditions | TOS (min) | C2H2 conversion rate (%) | Yield (%) | |
|---|---|---|---|---|
| | | | Aromatic compound | Total products |
| 400° C. ZSM-5 (Si/Al = 40) | 0 | 89.19 | 0.77 | 1.68 |

TABLE 5

| TOS (min) | $C_2H_2$ Conversion rate (%) | Selectivity (%) | | | | | | | | |
|---|---|---|---|---|---|---|---|---|---|---|
| | | $CH_4$ | $C_2H_6$ | $C_2H_4$ | $C_3H_8$ | $C_3H_6$ | benzene | toluene | xylene | unknown |
| 0 | 84.01 | 0.01 | 0 | 0.67 | 0 | 0.21 | 0.16 | 0.28 | 1.33 | 0.17 |

TABLE 6

| TOS (min) | $C_2H_2$ Conversion rate (%) | Yield (%) | | | | | | | | |
|---|---|---|---|---|---|---|---|---|---|---|
| | | $CH_4$ | $C_2H_6$ | $C_2H_4$ | $C_3H_8$ | $C_3H_6$ | benzene | toluene | xylene | unknown |
| 0 | 84.01 | 0 | 0 | 0.56 | 0 | 0.17 | 0.14 | 0.24 | 1.12 | 0.14 |

TABLE 7

| Temperature and specimen conditions | TOS (min) | C2H2 conversion rate (%) | Yield (%) | |
|---|---|---|---|---|
| | | | Aromatic compound | Total products |
| 400° C. HCZ-1 (Si/Al = 34) | 0 | 84.01 | 1.49 | 2.38 |

Comparing the results of Tables 2 to 4 with the results of Tables 5 to 7, when the ZSM-5 zeolite (HCZ-1) having a hierarchical structure according to the present invention was used, the yield of total products was increased, the yield of an aromatic compound was remarkably increased, and in particular, the selectivity and yield of xylene were increased seven-fold compared to when the conventional ZSM-5 was used.

What is claimed is:

1. A method for preparing an MFI zeolite with a microporous and mesoporous hierarchical structure in which an ordered microporous MFI zeolite additionally has mesopores, the method comprising:
   a first step of preparing a first aqueous solution in which a non-benzene-based first structure-directing agent, providing ordered microporous pore sizes and a framework of MFI zeolite seed crystals, is dissolved in water;
   a second step of preparing a second(2) aqueous solution in which a cationic surfactant, as a second structure-directing agent, containing one benzene ring and an ammonium ion connected to a bivalent alkyl group or alkoxy group, is dissolved in water;
   a third step of mixing an aluminum precursor with the second aqueous solution to prepare a second'(2') aqueous solution;
   a fourth step of sequentially adding a silica precursor and the second' aqueous solution to the first aqueous solution to prepare a mixed solution; and
   a fifth step of hydrothermally crystallizing the mixed solution obtained in the fourth step to form the MFI zeolite.

2. The method of claim 1, wherein the non-benzene-based first structure-directing agent is tetraalkylammonium hydroxide having a $C_{1-4}$ alkyl.

3. The method of claim 1, wherein the second structure-directing agent is a compound represented by Formula 1 below:

wherein, in Formula 1, X is Br, F, I, or Cl, L is —O— or a direct bond, and 1≤n≤6 is satisfied.

4. The method of claim 1, wherein the second structure-directing agent does not prevent the first structure-directing agent from providing a framework of MFI zeolite seed crystals of ordered microporous pore sizes, and serves as a mesopore-directing agent.

5. The method of claim 1, wherein the MFI zeolite with a microporous and mesoporous hierarchical structure is a cubic particle in which each side has a deviation of less than 10% in length.

6. The method of claim 1, wherein the MFI zeolite is a zeolite selected from the group consisting of ZSM-5, silicalite, TS-1, AZ-1, Bor-C, boracite C, encilite, FZ-1, LZ-105, monoclinic H-ZSM-5, mutenite, NU-4, NU-5, TSZ, TSZ-III, TZ-01, USC-4, USI-108, ZBH, and ZKQ-1B.

7. The method of claim 1, wherein the first structure-directing agent and the second structure-directing agent are used at a weight ratio of 1:(0.1 to 5).

8. The method of claim 1, wherein the silica precursor is tetraethyl orthosilicate (TEOS), glass water, fumed silica, or colloidal silica, and the aluminum precursor is sodium aluminate, aluminum isopropoxide, aluminum oxide, or aluminum hydroxide.

9. The method of claim 1, wherein the second structure-directing agent is benzyltrimethylammonium bromide (BTMAB).

10. The method of claim 9, wherein a molar ratio of tetraethyl orthosilicate as the silica precursor:sodium aluminate as the aluminum precursor:tetraalkylammonium hydroxide as the first structure-directing agent:benzyltrimethylammonium bromide as the second structure-directing agent:water is (30 to 35):(0.7 to 1.3):(5 to 10):(10 to 15):(1100 to 1200).

11. The method of claim 1, wherein the fifth step is performed at a temperature ranging from 150° C. to 250° C. for 12 hours to 48 hours.

12. An MFI zeolite with an ordered microporous and mesoporous hierarchical structure, in which an ordered microporous MFI zeolite additionally has mesopores, prepared by the method of claim 1.

13. The MFI zeolite of claim 12, wherein the non-benzene-based first structure-directing agent is tetraalkylammonium hydroxide having a $C_{1-4}$ alkyl.

14. The MFI zeolite of claim 12, wherein the second structure-directing agent is a compound represented by Formula 1 below:

wherein, in Formula 1, X is Br, F, I, or Cl, L is —O— or a direct bond, and 1≤n≤6 is satisfied.

15. A method of converting acetylene, the method comprising:
providing an acidic catalyst comprising the MFI zeolite of claim 12; and
contacting acetylene with the acidic catalyst to produce aromatic compounds.

16. The method of claim 15, wherein the aromatic compounds are benzene, toluene, or xylenes.

17. The method of claim 15, further comprising a step of converting the aromatic compounds by transalkylation, hydrocracking, esterification, or a combination thereof to produce a product.

* * * * *